US012755842B2

(12) United States Patent
Solomon et al.

(10) Patent No.: US 12,755,842 B2
(45) Date of Patent: Oct. 6, 2026

(54) METHODS AND SYSTEMS FOR IDENTIFYING A HEART CONDITION IN A NON-HUMAN SUBJECT USING PREDICTIVE MODELS

(71) Applicant: IDEXX Laboratories, Inc., Westbrook, ME (US)

(72) Inventors: Jessica Solomon, Westbrook, ME (US); Scott Bender, South Portland, ME (US); Caitlin Robar, Westbrook, ME (US); Suzanne Magoon, Westbrook, ME (US); Conrad Sastre, Westbrook, ME (US); Allison Spake, Westbrook, ME (US)

(73) Assignee: IDEXX LABORATORIES, INC., Westbrook, ME (US)

( * ) Notice: Subject to any disclaimer, the term of this patent is extended or adjusted under 35 U.S.C. 154(b) by 246 days.

(21) Appl. No.: 18/599,663

(22) Filed: Mar. 8, 2024

(65) Prior Publication Data

US 2024/0298989 A1 Sep. 12, 2024

Related U.S. Application Data

(60) Provisional application No. 63/489,220, filed on Mar. 9, 2023.

(51) Int. Cl.
*A61B 6/00* (2024.01)
*A61B 6/46* (2024.01)
(Continued)

(52) U.S. Cl.
CPC ............ *A61B 6/5217* (2013.01); *A61B 6/463* (2013.01); *A61B 6/503* (2013.01); *A61B 6/5247* (2013.01);
(Continued)

(58) Field of Classification Search
CPC ..... A61B 6/5217; A61B 6/5247; A61B 6/503; A61B 6/463; A61B 8/0883; A61B 8/463;
(Continued)

(56) References Cited

U.S. PATENT DOCUMENTS

2018/0116626 A1 5/2018 Darbari et al.
2020/0202527 A1 * 6/2020 Choi ...................... G16H 50/30
(Continued)

FOREIGN PATENT DOCUMENTS

WO 2020/257592 A1 12/2020

OTHER PUBLICATIONS

International Search Report and Written Opinion prepared by the European Patent Office in international application No. PCT/US24/019031 dated May 21, 2024.

*Primary Examiner* — Patricia J Park
(74) *Attorney, Agent, or Firm* — McDonnell Boehnen Hulbert & Berghoff LLP

(57) ABSTRACT

An example computer-implemented method for identifying a heart condition in a non-human subject includes receiving a medical image of the non-human subject, determining by a processor executing a first machine-learning logic and based on the medical image a dimensional feature of a heart of the non-human subject, displaying the dimensional feature of the heart on a graphical user interface, receiving medical information associated with the non-human subject on the graphical user interface, determining by the processor executing a second machine-learning logic and based on the medical information and the dimensional feature of the heart a likelihood of a heart disease, and displaying the likelihood of the heart disease on the graphical user interface.

19 Claims, 7 Drawing Sheets

(51) Int. Cl.

| | |
|---|---|
| ***A61B 6/50*** | (2024.01) |
| ***A61B 8/00*** | (2006.01) |
| ***A61B 8/08*** | (2006.01) |
| ***G06T 7/00*** | (2017.01) |
| ***G06T 7/62*** | (2017.01) |
| ***G06T 11/60*** | (2006.01) |
| ***G16H 50/20*** | (2018.01) |

(52) U.S. Cl.

CPC ............ *A61B 8/0883* (2013.01); *A61B 8/463* (2013.01); *A61B 8/5223* (2013.01); *A61B 8/5261* (2013.01); *G06T 7/0012* (2013.01); *G06T 7/62* (2017.01); *G06T 11/60* (2013.01); *G16H 50/20* (2018.01); *G06T 2200/24* (2013.01); *G06T 2207/20081* (2013.01); *G06T 2207/30048* (2013.01); *G06T 2210/41* (2013.01)

(58) Field of Classification Search

CPC ....... A61B 8/5223; A61B 8/5261; G06T 7/62; G06T 7/0012; G06T 11/60; G06T 2200/24; G06T 2207/20081; G06T 2207/30048; G06T 2210/41; G16H 50/20

See application file for complete search history.

(56) References Cited

U.S. PATENT DOCUMENTS

| | | | | |
|---|---|---|---|---|
| 2021/0232967 | A1* | 7/2021 | Nye | G06N 20/00 |
| 2021/0241914 | A1 | 8/2021 | Singer | |
| 2022/0351854 | A1* | 11/2022 | Li | G06N 3/0464 |
| 2023/0108955 | A1* | 4/2023 | Weissman | G16H 30/40<br>705/2 |
| 2023/0314449 | A1* | 10/2023 | Wilshaw | G16H 50/20<br>436/63 |

* cited by examiner

VERTEBRAL HEART SCORE

VERTEBRAL LEFT ATRIAL SIZE

METHODS AND SYSTEMS FOR IDENTIFYING A HEART CONDITION IN A NON-HUMAN SUBJECT USING PREDICTIVE MODELS

CROSS REFERENCE TO RELATED APPLICATION

The present disclosure claims priority to U.S. provisional application No. 63/489,220, filed on Mar. 9, 2023, the entire contents of which are herein incorporated by reference.

FIELD

The present disclosure relates generally to methods and systems for identifying a heart condition in a non-human subject.

BACKGROUND

A challenge lab technicians face when reviewing diagnostic test results and imaging of non-human subjects includes manual review, human errors or bias with interpretations, and possible lengthy review of individual cases. It is estimated that some labs may spend hundreds of hours (or more) a month reading and interpreting case files to develop a diagnosis. In addition, interpretation of case files can also require telemedicine services or input by further experts, presenting a strain on resources and delaying a full and correct diagnosis of the subject.

SUMMARY

In an example, a computer-implemented method for identifying a heart condition in a non-human subject is described comprising receiving a medical image of the non-human subject, determining, by a processor executing a first machine-learning logic and based on the medical image, a dimensional feature of a heart of the non-human subject and the first machine-learning logic is trained using medical image training data labeled with anatomical landmarks, receiving medical information associated with the non-human subject on a graphical user interface and the medical information including one or more of a species, an age, a weight, an output of a brain natriuretic peptide (BNP) test, and a murmur observation, determining, by the processor executing a second machine-learning logic and based on the medical information and the dimensional feature of the heart, a likelihood of a heart disease and the second machine-learning logic is trained using heart disease training data and combinations of which are labeled with different stages of heart disease, and displaying the likelihood of the heart disease on the graphical user interface.

In another example, a server is described comprising one or more processors, and non-transitory computer readable medium having stored therein instructions that when executed by the one or more processors, causes the server to perform functions. The functions comprises receiving a medical image of a non-human subject, determining, by the one or more processors executing a first machine-learning logic and based on the medical image, a dimensional feature of a heart of the non-human subject and the first machine-learning logic is trained using medical image training data labeled with anatomical landmarks, receiving medical information associated with the non-human subject on a graphical user interface, the medical information including one or more of a species, an age, a weight, an output of a brain natriuretic peptide (BNP) test, and a murmur observation, determining, by the one or more processors executing a second machine-learning logic and based on the medical information and the dimensional feature of the heart, a likelihood of a heart disease and the second machine-learning logic is trained using heart disease training data and combinations of which are labeled with different stages of heart disease, and displaying the likelihood of the heart disease on the graphical user interface.

In another example, a non-transitory computer readable medium is described having stored thereon instructions, that when executed by one or more processors of a computing device, cause the computing device to perform functions. The functions comprise receiving a medical image of the non-human subject, determining, by the one or more processors executing a first machine-learning logic and based on the medical image, a dimensional feature of a heart of the non-human subject and the first machine-learning logic is trained using medical image training data labeled with anatomical landmarks, receiving medical information associated with the non-human subject on a graphical user interface and the medical information including one or more of a species, an age, a weight, an output of a brain natriuretic peptide (BNP) test, and a murmur observation, determining, by the one or more processors executing a second machine-learning logic and based on the medical information and the dimensional feature of the heart, a likelihood of a heart disease and the second machine-learning logic is trained using heart disease training data and combinations of which are labeled with different stages of heart disease, and displaying the likelihood of the heart disease on the graphical user interface.

The features, functions, and advantages that have been discussed can be achieved independently in various examples or may be combined in yet other examples. Further details of the examples can be seen with reference to the following description and drawings.

BRIEF DESCRIPTION OF THE FIGURES

Examples and descriptions of the present disclosure will be readily understood by reference to the following detailed description of illustrative examples when read in conjunction with the accompanying drawings, wherein.

DETAILED DESCRIPTION

Figure 1:
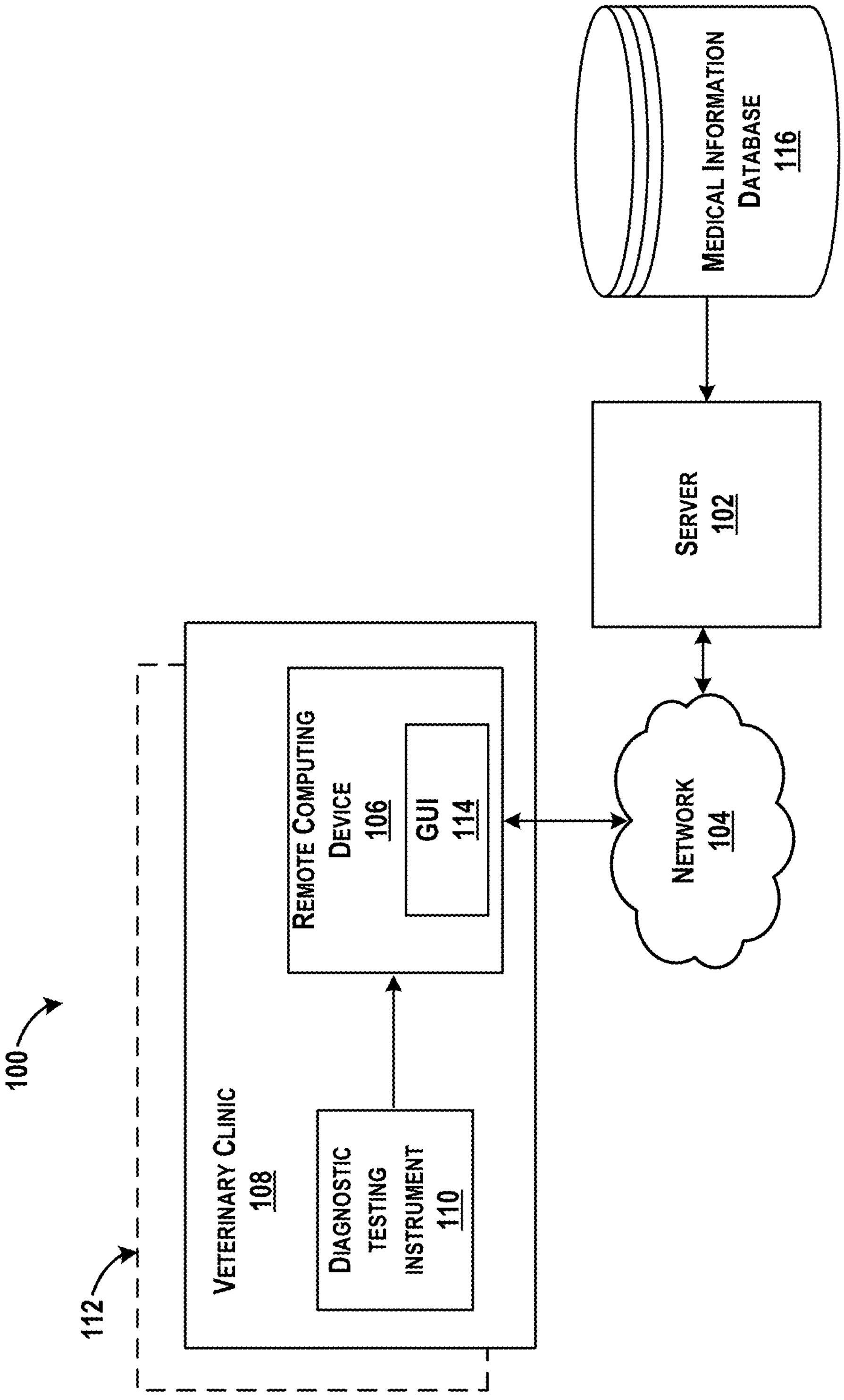
FIG. 1 illustrates an example of a system, according to an example implementation.

Disclosed examples will now be described more fully hereinafter with reference to the accompanying drawings. Several different examples are described herein, but embodiments should not be construed as limited to the examples set forth herein. Rather, these examples are described so that this disclosure will be thorough and complete and will fully convey the scope of the disclosure to those skilled in the art.

Existing processes for review of cases files includes manual review requiring hundreds of hours of work that presents strain on resources and can have inaccurate or incomplete results. Within examples herein, systems and methods provide executable machine-learning logic for automated image analysis (e.g., measurement of anatomical features in x-rays, such as heart measurements), display of measurements and other patient details, predictive modeling providing indications of a heart condition (e.g., suggest mitral valve disease diagnosis and staging), and tailored report creation.

Example systems and methods streamline reading of heart disease cases to increase efficiency and effectiveness of identifying heart conditions. The automated measurement tools (e.g., for both radiographs and echocardiograms) generate accurate and near-instant measurements of features of the heart, and these measurements are displayed in a viewer along with other relevant patient details from demographics, history, labwork, etc. The measurements and patient details are used are inputs to executable machine-learning logic to generate predictions about whether the patient is likely to have mitral valve disease, and if so, a staging of the disease.

Thus, an example computer-implemented method for identifying a heart condition in a non-human subject includes receiving a medical image of the non-human subject, and performing the automated measurements by a processor executing a first machine-learning logic to determine a dimensional feature of a heart of the non-human subject. Such dimensional features of the heart are displayed on a graphical user interface, and then the predictive modeling is run by the processor executing a second machine-learning logic using medical information of the patient and the dimensional feature of the heart to determine a likelihood of a heart disease.

Implementations of this disclosure thus provides technological improvements that are particular to computer technology, for example, those concerning analysis of imaging of a non-human subject for automated generation of measurements of anatomical features. Computer-specific technological problems, such as executing machine-learning logic in beneficial ways, can be wholly or partially solved by implementations of this disclosure. For example, implementation of this disclosure allows for x-rays and ultrasound images of a subject to be matched to labeled images using a machine-learning logic to identify features in the images so that measurements of the features can be made.

The systems and methods of the present disclosure further address problems particular to computer devices and operation of diagnostic instruments, for example, those concerning analysis of imaging and medical information about a patient. Utilizing machine-learning algorithms, trained on manually labeled data, enables a more immediate and normalized analysis of the data. Thus, analysis of the image and medical information can occur in a manner that is efficient and takes into account all patients' needs, and a predictive modeling approach offers summaries are in a manner to be immediately determined. Implementations of this disclosure can thus introduce new and efficient improvements in the ways in which data output from diagnostic instruments is analyzed to determine a likelihood of a heart disease in a subject.

Referring now to the figures, FIG. 1 illustrates an example of a system 100, according to an example implementation. The system 100 includes a server 102 accessible through a network 104 by multiple different computer systems. One set of the computer systems includes a remote computing device 106 residing at a veterinary clinic 108 that also includes a diagnostic testing instrument 110 to perform diagnostic testing of veterinary patients, for example. The diagnostic testing instrument 110 outputs diagnostic test results to the remote computing device 106 for analysis. While one veterinary clinic 108 is depicted in FIG. 1, it should be understood that this is merely an example, and systems according to the present disclosure can include any suitable number of veterinary clinics and associated computer systems, such as a second veterinary clinic 112 that includes the same or similar components as the veterinary clinic 108. As referred to herein, the term "veterinary clinics" includes any entity at which non-human animals receive medical care, and can include brick and mortar locations, mobile clinics, on-line virtual clinics, pop-up clinics, and the like.

In addition, while the example depicted in FIG. 1 includes one diagnostic testing instrument 110, it should be understood that this is merely an example, and embodiments according to the present disclosure can include any suitable number of diagnostic testing instruments associated with the veterinary clinic 108. Examples of the diagnostic testing instrument 110 include any one or combination of veterinary analyzers operable to conduct a diagnostic test of a sample of a patient (e.g., operable to determine hemoglobin amounts in a blood sample, operable to analyze a urine sample, and/or the like). Such veterinary analyzers include, for example and without limitation, a clinical chemistry analyzer, a hematology analyzer, a urine analyzer, an immunoassay reader, a sediment analyzer, a blood analyzer, a digital radiology machine, and/or the like. In one example, the remote computing device 106 is in communication with a veterinary analyzer of the diagnostic testing instrument 110 and is operable to receive diagnostic information from veterinary analyzer. The diagnostic testing instrument 110 outputs signals, such as signals indicative of diagnostic test results or other information, to the remote computing device 106.

In the system 100, the network 104 (e.g., Internet) provides access to the server 102 for all network-connected components. In some examples, more components of the system 100 may be in communication with the network 104 to access the server 102. Communication with the server 102 and/or with the network 104 may be wired or wireless communication (e.g., some components may be in wired Ethernet communication and others may use Wi-Fi communication). In still further examples, the network 104 provides access for the server 102 to communicate with the remote computing device 106 directly as well.

The system 100 enables a method for identifying a heart condition in a non-human subject, for example. The server 102 receives a medical image of the non-human subject, such as an x-ray taken by the diagnostic testing instrument 110 and then sent by the remote computing device 106 over the network 104. The server 102 then executes machine-learning logic to determine a dimensional feature of a heart of the non-human subject on the image and executes machine-learning logic on medical information of the subject and the dimensional feature of the heart to determine a likelihood of a heart disease. In some examples, these functions are performed all by the remote computing device 106 without the aid of the server 102.

The remote computing device 106, in embodiments, includes a graphical user interface (GUI) 114 for display, which is operable to receive input data to send to the server 102 (e.g., data associated with the subject such as breed, age, etc.). The GUI 114 is thus operable to receive inputs to the remote computing device 106, and to provide an updated display that displays the dimensional feature of the heart on an interface of the GUI 114, and displays the likelihood of the heart disease on the interface of the GUI 114.

The system 100, in embodiments, includes a medical information database 116 to which the server 102 is in communication for retrieving corresponding medical information of the subject. Example medical information associated with the non-human subject that is stored in the medical information database 116 includes one or more of a species, an age, a weight, an output of a brain natriuretic peptide (BNP) test, and a murmur observation. Any information captured during a visit to the clinic by the subject can be input into the medical information database 116.

In some examples, the remote computing device 106 has access to the medical information database 116, such as via the network 104.

Figure 2:
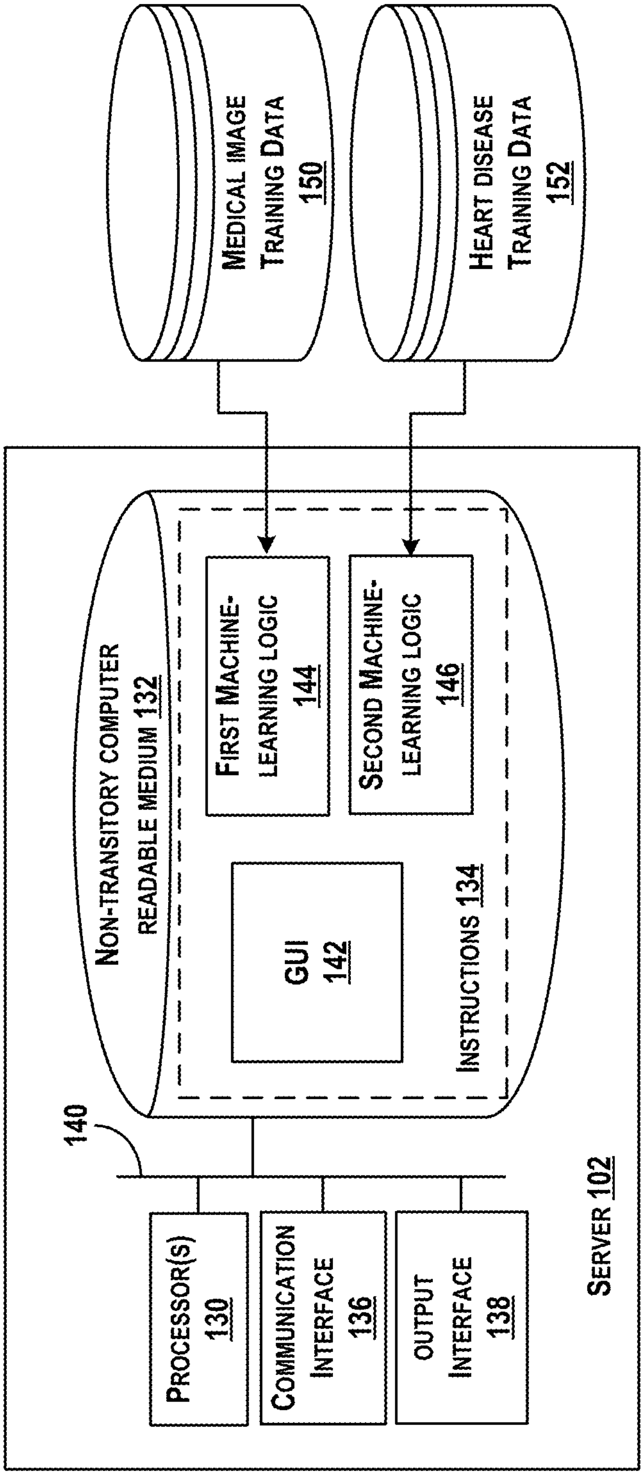
FIG. 2 illustrates an example of the server in FIG. 1, according to an example implementation.

FIG. 2 illustrates an example of the server 102 in FIG. 1, according to an example implementation. Within examples herein, functions described for identifying a heart condition in a non-human subject are performed by the remote computing device 106, by the server 102, or by a combination of the remote computing device 106 and the server 102. Thus, although FIG. 2 illustrates the server 102, the components of the remote computing device 106 are the same as the components of the server 102 within some examples, depending on where a function is programmed to be performed in a specific implementation.

The server 102 includes one or more processor(s) 130, and non-transitory computer readable medium 132 having stored therein instructions 134 that when executed by the one or more processor(s) 130, causes the server 102 to perform functions for processing diagnostic test result data, as well as management and control of diagnostic testing instruments 110 (FIG. 1) and for generation of inquiries for display on a GUI such as GUI 114 (FIG. 1), for example.

To perform these functions, the server 102 also includes a communication interface 136, an output interface 138, and components of the server 102 are connected to a communication bus 140. The server 102 may also include hardware to enable communication within the server 102 and between the server 102 and other devices (not shown). The hardware may include transmitters, receivers, and antennas, for example. The server 102 may further include a display (not shown).

The communication interface 136 may be a wireless interface and/or one or more wireline interfaces that allow for both short-range communication and long-range communication to one or more networks or to one or more remote devices. Such wireless interfaces may provide for communication under one or more wireless communication protocols, Bluetooth, WiFi (e.g., an institute of electrical and electronic engineers (IEEE) 802.11 protocol), Long-Term Evolution (LTE), cellular communications, near-field communication (NFC), and/or other wireless communication protocols. Such wireline interfaces may include an Ethernet interface, a Universal Serial Bus (USB) interface, or similar interface to communicate via a wire, a twisted pair of wires, a coaxial cable, an optical link, a fiber-optic link, or other physical connection to a wireline network. Thus, the communication interface 136 may be configured to receive input data from one or more devices, and may also be configured to send output data to other devices.

The non-transitory computer readable medium 132 includes or takes the form of memory, such as one or more computer-readable storage media that can be read or accessed by the one or more processor(s) 130. The non-transitory computer readable medium 132 can include volatile and/or non-volatile storage components, such as optical, magnetic, organic or other memory or disc storage, which can be integrated in whole or in part with the one or more processor(s) 130. In some examples, the non-transitory computer readable medium 132 is implemented using a single physical device (e.g., one optical, magnetic, organic or other memory or disc storage unit), while in other examples, the non-transitory computer readable medium 132 is implemented using two or more physical devices. The non-transitory computer readable medium 132 thus is a computer readable storage, and the instructions 134 are stored thereon. The instructions 134 include computer executable code.

The one or more processor(s) 130 may be general-purpose processors or special purpose processors (e.g., digital signal processors, application specific integrated circuits, etc.). The one or more processor(s) 130 receive inputs from the communication interface 136 (e.g., x-ray images), and process the inputs to generate outputs that are stored in the non-transitory computer readable medium 132. The one or more processor(s) 130 are configured to execute the instructions 134 (e.g., computer-readable program instructions) that are stored in the non-transitory computer readable medium 132 and are executable to provide the functionality of the server 102 described herein.

The output interface 138 outputs information for transmission, reporting, or storage, and thus, the output interface 138 may be similar to the communication interface 136 and can be a wireless interface (e.g., transmitter) or a wired interface as well.

Within examples, the instructions 134 include specific software for performing the functions including a GUI 142, a first machine-learning logic 144, and a second machine-learning logic 146.

With respect to the GUI 142, the server 102 includes a display to display information. In examples where FIG. 2 represents the remote computing device 106, the GUI 142 may be the same as the GUI 114 in FIG. 1 for receiving information from the server 102 for display on the GUI.

The first machine-learning logic 144 and the second machine-learning logic 146 are each selectable for execution based on a type of information that is received at the server 102. In one example, each initial data received at the server 102 from the remote computing device 106 includes an identifier, for example, of a type of diagnostic testing instrument that output the data. The server 102 selects one of the first machine-learning logic 144 or the second machine-learning logic 146 for execution based on the type of diagnostic data and/or type of diagnostic testing instrument that output the data.

Although two different machine-learning logic 144 and 146 are shown, the server 102 and the instructions 134 may include more or fewer machine-learning logic for different testing instrumentation.

Each of the first machine-learning logic 144 and the second machine-learning logic 146 are trained using specific training data. As shown in FIG. 2, the first machine-learning logic 144 is trained using medical image training data 150 that includes subject images (x-rays, ultrasound images, electrocardiogram (ECG) images, etc.) with organs and features of organs (e.g., the heart and associated blood vessels) labeled in the images to denote anatomical landmarks. The second machine-learning logic 146 is trained using heart disease training data 152 that includes different combinations of information which are labeled with different stages of heart disease. The combinations of information includes measurements of features of the heart, a species, an age, a weight, an output of a brain natriuretic peptide (BNP) test, and a murmur observation of subjects and associated stages of a heart disease.

In one example operation, the server 102 receives from the remote computing device 106 (FIG. 1) a medical image of the non-human subject and determines, by the processor 130 executing the first machine-learning logic 144 and based on the medical image, a dimensional feature of a heart of the non-human subject. The server 102 can then display or provide for display on the remote computing device 106 the dimensional feature of the heart on the GUI 114 or 142. Following, the server 102 receives medical information associated with the non-human subject on the GUI 114 and/or 142, such as species, an age, a weight, an output of a brain natriuretic peptide (BNP) test, and a murmur observation, and determines, by the processor 130 executing the second machine-learning logic 146 and based on the medical information and the dimensional feature of the heart, a likelihood of a heart disease. The server 102 then displays or provides for display by the remote computing device 106 the likelihood of the heart disease on the GUI 114 and/or 142.

In another example operation, the remote computing device 106 performs all functions and receives from the diagnostic testing instrument 110 a medical image of the non-human subject and determines, by the processor 130 executing the first machine-learning logic 144 and based on the medical image, a dimensional feature of a heart of the non-human subject. The remote computing device 106 then displays the dimensional feature of the heart on the GUI 114 and/or 142. Following, the remote computing device 106 receives medical information associated with the non-human subject on the GUI 114 and/or 142, such as species, an age, a weight, an output of a brain natriuretic peptide (BNP) test, and a murmur observation, and determines, by the processor 130 executing the second machine-learning logic 146 and based on the medical information and the dimensional feature of the heart, a likelihood of a heart disease. The remote computing device 106 then displays the likelihood of the heart disease on the GUI 142.

Execution of the first machine-learning logic 144 and the second machine-learning logic 146 to perform analysis of the medical imaging and information removes any human pathologist bias and generates normalized results for all inputs.

Referring to the first machine-learning logic 144 and the second machine-learning logic 146, many types of functionality and neural networks can be employed to perform functions of specific machine-learning algorithms to carry out functionality described herein. In one example, the first machine-learning logic 144 and the second machine-learning logic 146 use statistical models to generate outputs without using explicit instructions, but instead, by rely on patterns and inferences by processing associated training data.

The first machine-learning logic 144 and the second machine-learning logic 146 can thus operate according to machine-learning tasks as classified into several categories. In supervised learning, the first machine-learning logic 144 and the second machine-learning logic 146 build a mathematical model from a set of data that contains both the inputs and the desired outputs. The set of data is sample data known as the "training data", in order to make predictions or decisions without being explicitly programmed to perform the task. For example, the first machine-learning logic 144 and the second machine-learning logic 146 utilize the medical image training data 150 and the heart disease training data 152 within comparisons to identify matches of features in received images to the labeled anatomical landmarks within a threshold. When such a match is found, the labeled training data is reference as a label to be applied to the received image data.

In another category referred to as semi-supervised learning, the first machine-learning logic 144 and the second machine-learning logic 146 develop mathematical models from incomplete training data, where a portion of the sample input does not have labels. A classification algorithm can then be used when the outputs are restricted to a limited set of values.

In another category referred to as unsupervised learning, the first machine-learning logic 144 and the second machine-learning logic 146 builds a mathematical model from a set of data that contains only inputs and no desired output labels. Unsupervised learning algorithms are used to find structure in related training data, such as grouping or clustering of data points. Unsupervised learning can discover patterns in data, and can group the inputs into categories.

Alternative machine-learning algorithms may be used to learn and classify types of images and medical information to consider for generating the prediction of a heart disease, such as deep learning though neural networks or generative models. Deep machine-learning may use neural networks to analyze prior test results through a collection of interconnected processing nodes. The connections between the nodes may be dynamically weighted. Neural networks learn relationships through repeated exposure to data and adjustment of internal weights. Neural networks may capture nonlinearity and interactions among independent variables without pre-specification. Whereas traditional regression analysis requires that nonlinearities and interactions be detected and specified manually, neural networks perform the tasks automatically.

Still other machine-learning algorithms or functions can be implemented to identify anatomical features in images and determine a prediction of a heart disease, such as any number of classifiers that receives input parameters and outputs a classification (e.g., attributes of the image). Support vector machine, Bayesian network, a probabilistic boosting tree, neural network, sparse auto-encoding classifier, or other known or later developed machine-learning algorithms or any suitable combination thereof may be used. Any semi-supervised, supervised, or unsupervised learning may be used. Hierarchal, cascade, or other approaches may be also used.

The first machine-learning logic 144 and the second machine-learning logic 146 may thus be considered an application of rules in combination with learning from prior labeled data to identify appropriate outputs. Analyzing and relying on prior labeled data allows the first machine-learning logic 144 and the second machine-learning logic 146 to apply patterns of images and medical information associated with a likelihood of heart disease, for example.

Thus, the first machine-learning logic 144 and the second machine-learning logic 146 take the form of one or a combination of any of the machine-learning algorithms described herein, for example.

Figure 3:
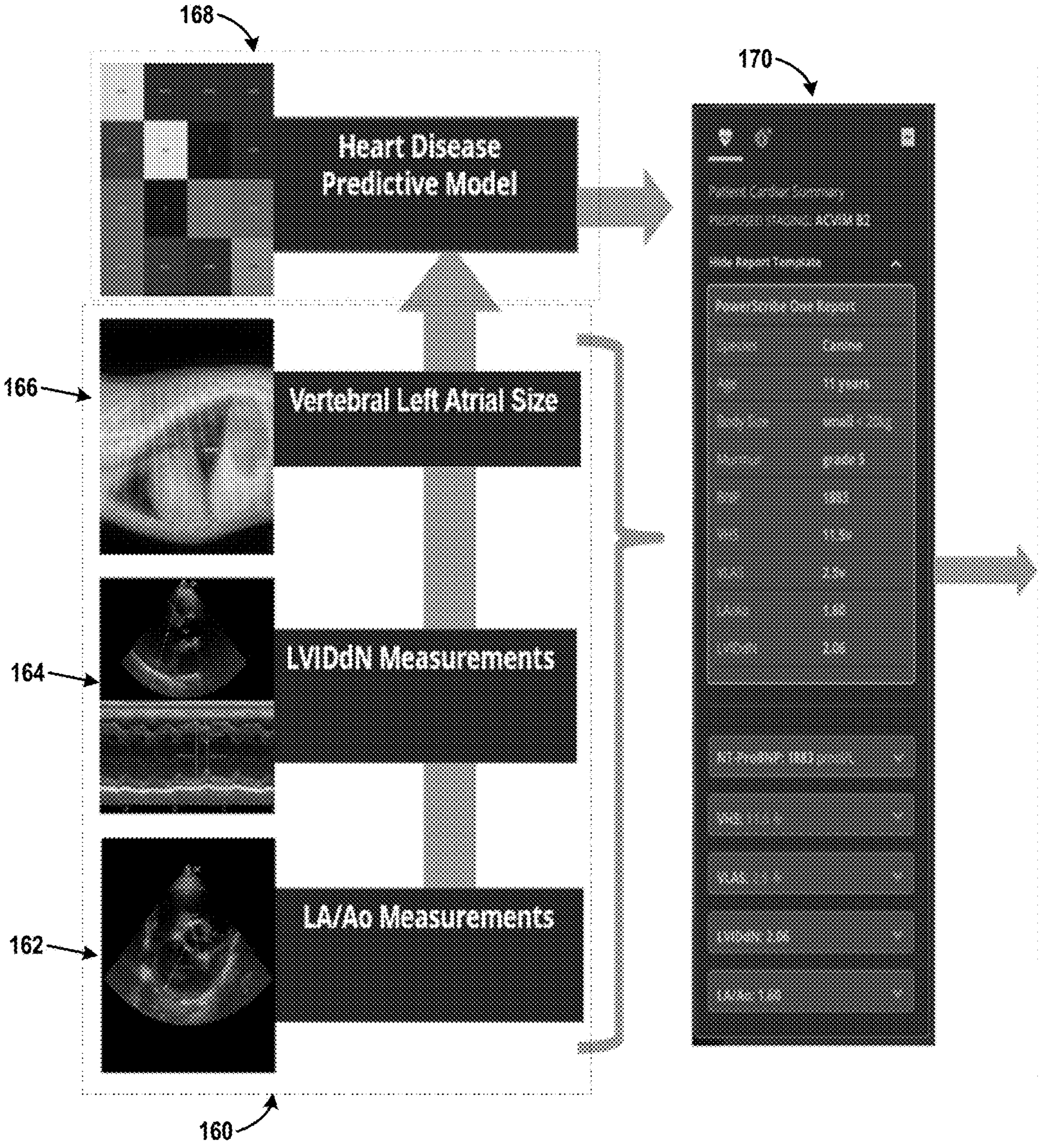
FIG. 3 is a block diagram illustrating an example workflow for identifying a heart condition in a non-human subject, according to an example implementation.

FIG. 3 is a block diagram illustrating an example workflow for identifying a heart condition in a non-human subject, according to an example implementation. As mentioned, initially, a medical image of the non-human subject is received. In FIG. 3, medical imaging 160 is shown to include many possible variations, such as ultrasound images 162 and 164 and radiograph images 166, for example. The server 102 (FIG. 2) executes the first machine-learning logic 144 to determine a dimensional feature of a heart of the non-human subject based on the medical image. For example, the first machine-learning logic 144 is trained using medical image training data 150 (FIG. 2) labeled with anatomical landmarks and objects in the medical image are identified as features of the heart through image analysis and comparison with the labeled training data. Upon identifying the features of the heart in the medical image, measurement calculations of the features can be made to determine the dimensional feature of the heart.

Many different types of measurements are useful as factors to consider for identifying a heart condition. Example dimensional features of the heart to determine based on measurement calculations include a left atrial to aortic ratio (LA/Ao) measurement, a left ventricular internal diameter at end-diastole (LVIDdN) measurement, and a ventricular left atrial size (VLAS) measurement. Other dimensional features of the heart to determine based on measurement calculations can include a vertebral heart scale (VHS) and an atrial measurement, for example.

The determined dimensional features are input into the heart disease predictive model 168, and functions of the heart disease predictive model 168 are performed by the processor 130 executing the second machine-learning logic 146. The heart disease predictive model 168 is trained on dimensional data (e.g., LA/Ao, LVIDdN, VLAS, etc.) to predict different stages of heart disease per patient using additional patient data (e.g., age, body size, breed, etc.).

An output of the heart disease predictive model 168 is a prediction of a likelihood of a heart disease by the patient, such as a likelihood of a mitral valve disease and a stage of the heart disease. The output is provided in a report 170 that includes a summary of pertinent data analyzed by the heart disease predictive model 168 (e.g., dimensional measurements, patient data, etc.) along with a VHS. The report 170 is provided in the GUI 142 (FIG. 2) and/or GUI 114 (FIG. 1), such that items in the report 170 are selectable to expand, display graphs for trending, display normal ranges, flag abnormal results, and apply trend lines across time for multiple measurements to observe stable or progressing disease.

Figure 4:
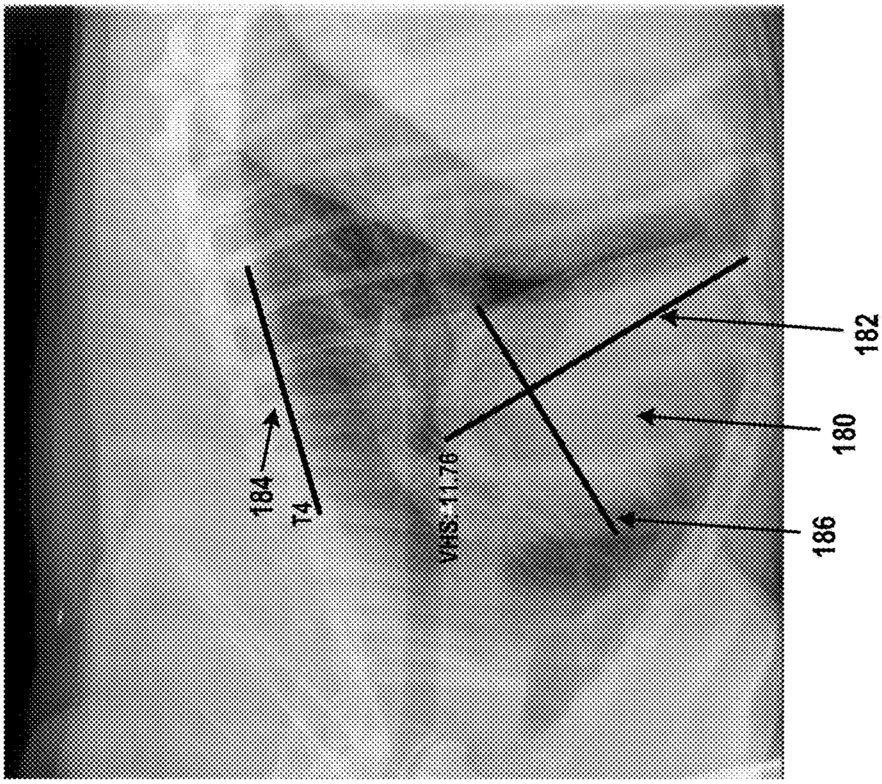
FIG. 4 is an example radiograph image of a subject showing measurement calculations overlaid onto the image, according to an example implementation.

FIG. 4 is an example radiograph image of a subject showing measurement calculations overlaid onto the image, according to an example implementation. In FIG. 4, dimensional features of a heart 180 are measured to calculate a VHS. First, a longest axis of the cardiac silhouette is measured designated as line 182, and this measurement is transferred to the vertebrae as shown by line 184 to count a number of vertebrae that fall within the points of the line. Following, a short axis across a widest part of the cardiac silhouette perpendicular to the long axis measurement is made as shown by line 186 and this line is also transferred to the vertebrae to count the number of vertebrae that fall within the points of the line. The sum of those measurements is the VHS (e.g., in FIG. 4, VHS=L+S=5.2+4.4=9.6, which is in a normal range). The radiograph is displayed to include as graphical images the lines 182, 184, and 186 overlaid onto the radiograph image.

To make the measurements shown in FIG. 4, after anatomical landmarks of the heart 180 are determined by executing the first machine-learning logic 144, the processor 130 determines a distance between pixel points on the radiograph image between the identified anatomical landmarks of the heart and vertebrae. Such distance measurements between pixel points can be normalized to a size of the subject to be applied to reference data.

Figure 5:
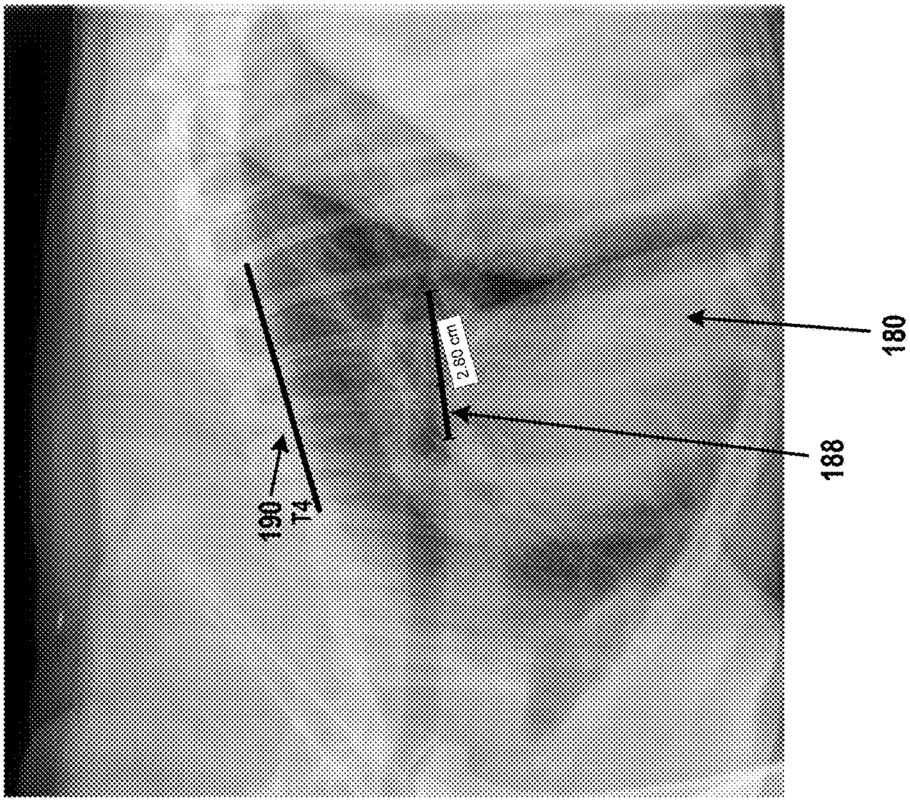
FIG. 5 is another example radiograph image of a subject showing measurement calculations overlaid onto the image, according to an example implementation.

FIG. 5 is another example radiograph image of a subject showing measurement calculations overlaid onto the image, according to an example implementation. In FIG. 5, dimensional features of the heart 180 are measured to calculate the VLAS. The VLAS measures a left atrial size on a right lateral projection. To perform the measurement, after the first machine-learning logic 144 is executed to identify anatomical landmarks in the image, measurements are made from pixel points representing a ventral margin of the carina to where the dorsal border of caudal vena cava and caudal cardiac silhouette intersect, and the measurement is designated as line 188 in FIG. 5. Next, the measurement is scaled against a length of the vertebrae dorsal to the heart 180 starting from a cranial aspect of the fourth vertebra (T4) as designated by line 190, to count the number of vertebrae that fall within the points of the line. If the measurement is higher than 2.3, the VLAS may be indicative of left atrial enlargement.

In FIGS. 4-5, the measurements are illustrated in the GUI 142 (FIG. 2) and/or GUI 114 (FIG. 1) by overlaying graphical lines onto the radiograph images, as shown. Additional graphics are also included, in some examples, such as illustrating the VHS in FIG. 4 as a digital graphic overlaid onto the radiograph or illustrating the measurement calculation amount in FIG. 5 as a digital graphic overlaid onto the radiograph.

Figure 6:
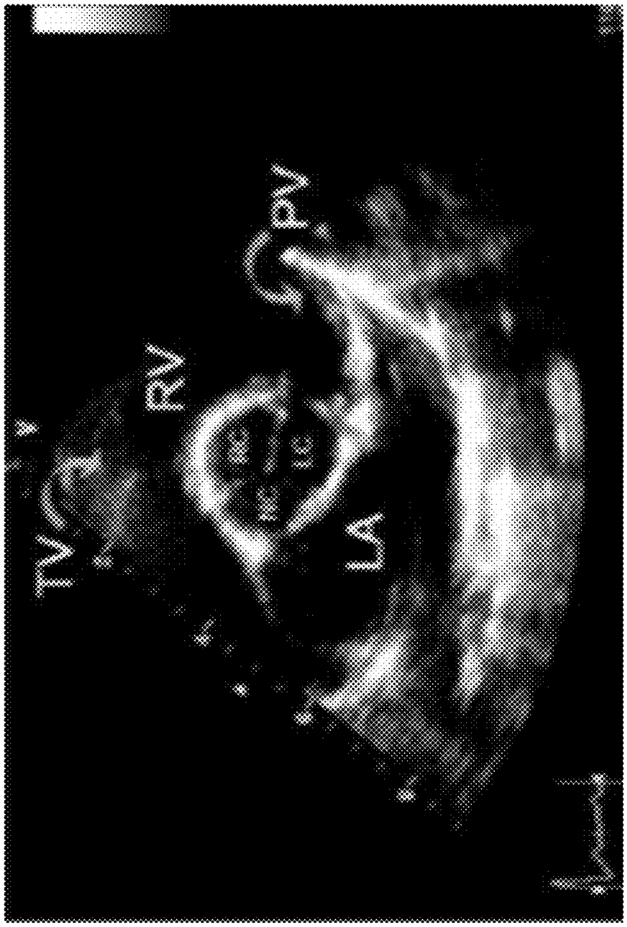
FIG. 6 is an example ultrasound image of a subject showing measurement calculations overlaid onto the image, according to an example implementation.

FIG. 6 is an example ultrasound image of a subject showing measurement calculations overlaid onto the image, according to an example implementation. In FIG. 6, measurements are made to obtain the LA/Ao measurement. To perform the measurement, after the first machine-learning logic 144 (FIG. 2) is executed to identify anatomical landmarks in the image, measurements are made from pixel points representing the left atrial and aorta. In FIG. 6, the right ventricle (RV), tricuspid valve (TV), and pulmonary valve (PV) are labeled, and then the short-axis diameter of the aorta is measured along the commissure between the noncoronary and right coronary aortic valve cusps on a first frame after aortic valve closure followed by measuring a short-axis diameter of the LA in the same frame in a line extending from and parallel to the commissure between the noncoronary and left coronary aortic valve cusps to the distant margin of the left atrium. Then, once the measurements are made, the ratio LA/Ao is computed.

Figure 7:
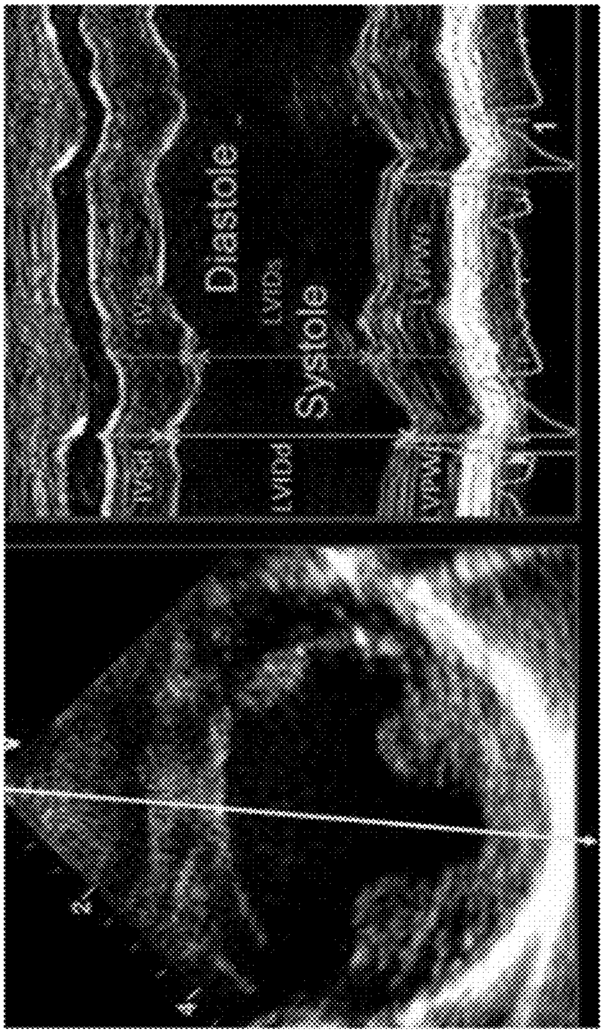
FIG. 7 is another example ultrasound image of a subject showing measurement calculations overlaid onto the image, according to an example implementation.

FIG. 7 is another example ultrasound image of a subject showing measurement calculations overlaid onto the image, according to an example implementation. In FIG. 7, to perform the measurements, after the first machine-learning logic 144 (FIG. 2) is executed to identify anatomical landmarks in the image, measurements are made from pixel points representing different portions of the heart to obtain IVSd (interventricular septal end diastole), IVSs (interventricular septal end systole), LVIDd (left ventricular internal diameter end diastole), LVIDs (left ventricular internal diameter end systole), PWd (posterior wall end diastole), and PWs (posterior wall end systole). Graphics are overlaid onto the ultrasound image after the measurements are made, as shown in FIG. 7.

In FIGS. 2 and 4-7, as mentioned, to perform the measurements the first machine-learning logic 144 is executed to identify anatomical landmarks in the image. Then, the processor 130 executes the instructions 134 to programmatically determine or calculate distances between pixel points in the images, determined to be representative of features of the heart for which a respective measurement is being made. Following calculation of the distances, the processor 130 executes the instructions 134 to programmatically insert graphical/digital lines, representing the calculated measurements, overlaid onto the images. Thus, the determination of features of the heart as well as measurement calculations are both programmatically performed by the processor 130 executing the instructions 134 including execution of the first machine-learning logic 144.

Referring back to FIGS. 2 and 3, once the dimensional features of the heart have been made, the calculations are input to the heart disease predictive model 168 to determine a prediction of a likelihood of a heart disease by the patient. To make the prediction, the processor 130 executes the second machine-learning logic 146, which has been trained using the heart disease training data 152 that has calculations of heart measurements with associated subject data arranged in a matrix configuration, for example. The second machine-learning logic 146 is executed to identify which permutation of stored data most closely matches input data to relate a diagnosis of the matched stored data to the input data.

Data input to the heart predictive model 168 can thus include species (e.g., canine), age (e.g., young or old (e.g., >4 years), body size (e.g., small breed <20 kg), murmur (e.g., none, soft, loud), BNP (e.g., less than or greater than 900), VHS (less than 11.1/11.5 or higher), VLAS (less than 2.3; 2.3-2.8; or greater than 2.8), LA/Ao (less than or greater than 1.6), LViDdN (less than or greater than 1.7), and echo visualization of deformed valves/documentation of regurgitation with Doppler.

An output of the predictive model 168 is a summary report with a predictive analysis. Thus, a structured report is output for a mitral valve disease dog using automated VHS and adding VHS to the report so parameters are all shown, and the same can be performed with VLAS to be used in combination with age, weight, etc., to generate a complete report for a predictive diagnosis of a B1 or B2 mitral valve disease dog. Within the report 170, the measurements are pre-populated and access to the images used to calculate the measurements are enabled through drop-down menus where the measurements are shown with graphical overlays (e.g., as illustrated in FIGS. 4-7).

An example of a predictive analysis includes a patient that is a small breed dog with a loud heart murmur, and the VHS and VLAS is obtained from radiographs and/or left atrial and left ventricular size from echo images. From patient data and these measurements, the processor 130 executes the second machine-learning logic 146 to generate a structured report including a prediction of a likelihood of heart disease and a disease stage, where information in the report is populated.

Within examples, different heart diseases are evaluated within the heart disease predictive model 168. Examples of heart diseases considered include mitral valve heart disease and dilated cardiomyopathy (DCM). For instance, for DCM, the heart disease prediction considers body weight, murmur, VHS, VLAS, LA/Ao, and Left Ventricular Internal Diameter normalized dimensions (LVIDDn), and DCM is diagnosed when body weight is greater than 20 kg, a murmur is greater than grade 3, and fractional shortening (part of the LV echo measurement tool) is less than 20%.

For mitral valve heart disease, in addition to making a prediction of a likelihood of the subject having mitral valve disease, the second-machine learning logic 146 is executable to estimate a stage of the disease. Parameters considered in the heart disease training data 152 for determination of different stages include: Stage A (subject at high risk for developing heart disease); Stage B1 (subject with valvular regurgitation but no cardiac dilation); Stage B2 (subject with valvular regurgitation and cardiac dilation); Stage C (subject with valvular regurgitation, cardiac dilation and congestive heart failure); Stage D (stage C subject with recurrent/refractory heart failure). Thus, when displaying the likelihood of the heart disease on the GUI 142 (FIG. 2) and/or GUI 114 (FIG. 1) in the report 170, a prediction of a stage of the heart disease along with a summary of the dimensional feature of the heart is included.

Figure 8:
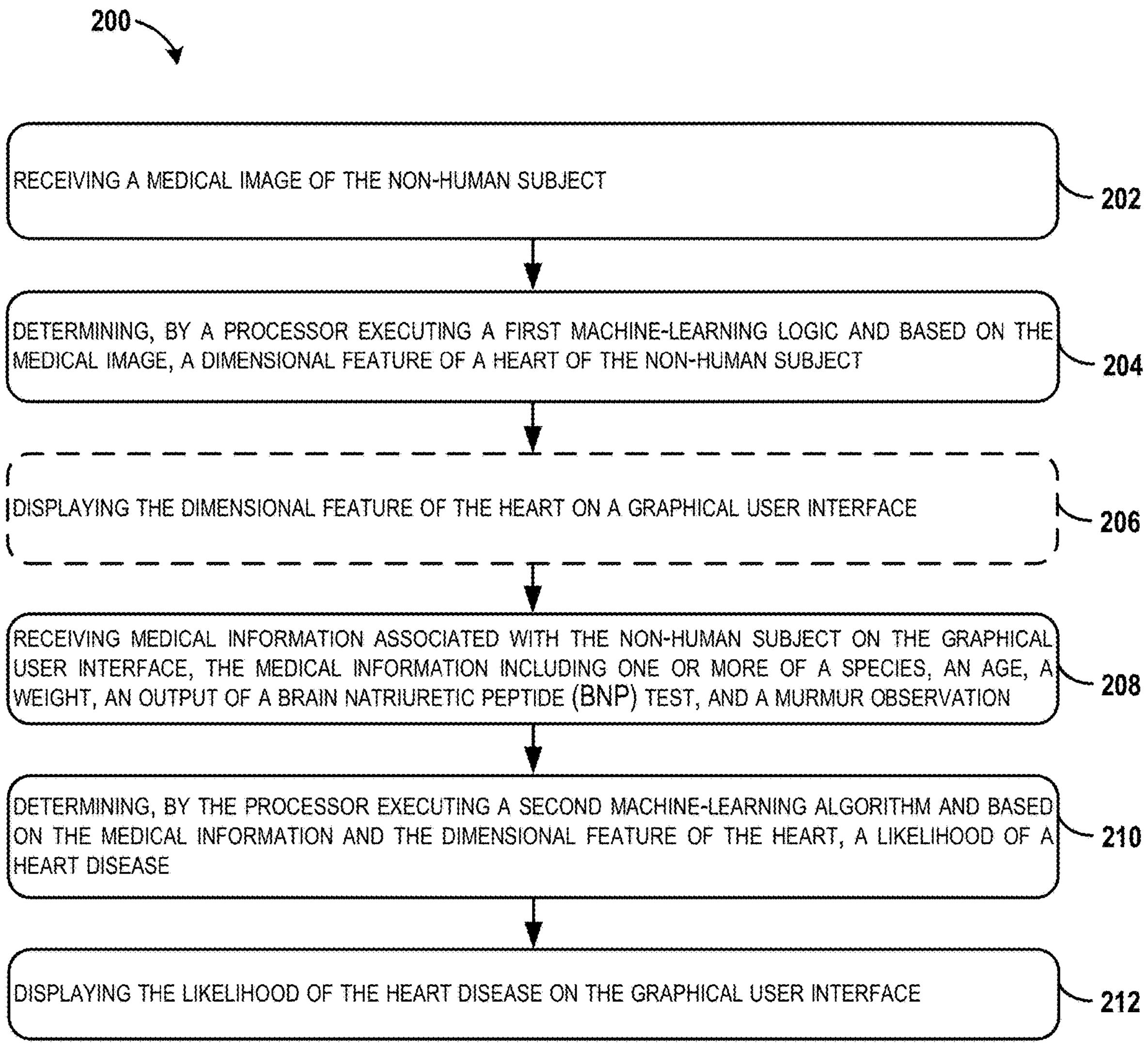
FIG. 8 shows a flowchart of an example of a method for identifying a heart condition in a non-human subject, according to an example implementation.

FIG. 8 shows a flowchart of an example of a method 200 for identifying a heart condition in a non-human subject, according to an example implementation. Method 200 shown in FIG. 8 presents an example of a method that could be used with the system 100 shown in FIG. 1, the server 102 shown in FIG. 1, and/or the remote computing device 106 shown in FIG. 1, for example. Further, devices or systems may be used or configured to perform logical functions presented in FIG. 8. In some instances, components of the devices and/or systems may be configured to perform the functions such that the components are actually configured and structured (with hardware and/or software) to enable such performance. In other examples, components of the devices and/or systems may be arranged to be adapted to, capable of, or suited for performing the functions, such as when operated in a specific manner. Method 200 may include one or more operations, functions, or actions as illustrated by one or more of blocks 202-212. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

It should be understood that for this and other processes and methods disclosed herein, flowcharts show functionality and operation of one possible implementation of present examples. In this regard, each block or portions of each block may represent a module, a segment, or a portion of program code, which includes one or more instructions executable by a processor for implementing specific logical functions or steps in the process. The program code may be stored on any type of computer readable medium or data storage, for example, such as a storage device including a disk or hard drive. Further, the program code can be encoded on a computer-readable storage media in a machine-readable format, or on other non-transitory media or articles of manufacture. The computer readable medium may include non-transitory computer readable medium or memory, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a tangible computer readable storage medium, for example.

In addition, each block or portions of each block in FIG. 8, and within other processes and methods disclosed herein, may represent circuitry that is wired to perform the specific logical functions in the process. Alternative implementations are included within the scope of the examples of the present disclosure in which functions may be executed out of order from that shown or discussed, including substantially concurrent or in reverse order, depending on the functionality involved, as would be understood by those reasonably skilled in the art.

At block 202, the method 200 includes receiving a medical image of the non-human subject. In one example, receiving the medical image comprises receiving one or more of an echocardiogram, an x-ray, a radiograph, and an ultrasound image.

At block 204, the method 200 includes determining, by a processor executing a first machine-learning logic and based on the medical image, a dimensional feature of a heart of the non-human subject and the first machine-learning logic is trained using medical image training data labeled with anatomical landmarks. In one example, determining the dimensional feature of the heart comprises determining features in the medical image matching to the anatomical landmarks in the labeled training data, and performing a measurement calculation between selected features in the medical image. Within examples, the dimensional feature of the heart includes one or more of a vertebral heart score, an atrial measurement, a ventricular left atrial size (VLAS) measurement, a vertebral heart scale (VHS), a left atrial to aortic ratio (LA/Ao) measurement, and a left ventricular internal diameter at end-diastole (LVIDdN) measurement. Within examples, the vertebral heart score, vertebral heart size, and the VHS are considered the same metric based on a viewpoint of the measurements being made, and reference to these terms herein refers to the same metric.

At block 206, the method 200 optionally includes displaying the dimensional feature of the heart on a graphical user interface. In one example, displaying the dimensional feature of the heart on the graphical user interface comprises displaying the dimensional feature of the heart as a digital graphic overlaying the medical image on the graphical user interface.

At block 208, the method 200 includes receiving medical information associated with the non-human subject on the graphical user interface, the medical information including one or more of a species, an age, a weight, an output of a brain natriuretic peptide (BNP) test, and a murmur observation.

At block 210, the method 200 includes determining, by the processor executing a second machine-learning logic and based on the medical information and the dimensional feature of the heart, a likelihood of a heart disease, and the second machine-learning logic is trained using heart disease training data and combinations of which are labeled with different stages of heart disease. In one example, determining the likelihood of the heart disease comprises determining a likelihood of a mitral valve disease, and determining a stage of the heart disease.

At block 212, the method 200 includes displaying the likelihood of the heart disease on the graphical user interface. In one example, displaying the likelihood of the heart disease on the graphical user interface comprises displaying a prediction of a stage of the heart disease, displaying a summary of the dimensional feature of the heart, and displaying interactive menus selectable to modify the graphical user interface to display a graph for trend analysis.

Within example systems and methods described herein, advantages and improvements over existing methods include utilization of normalized measurement processes (in contrast to manual use of a basic ruler tool for measuring dimensions of the heart, for which many variations are possible due to different ruler tools and user bias), integration of electronic information from several different sources such as patient demographics, case history, bloodwork results and the image viewer, and a highly detailed structured report including individual transcription of cardiac measurements.

With reference to FIG. 2, and throughout the disclosure, some components are described as "modules," "engines", "models", or "generators" and such components include or take a form of a general purpose or special purpose hardware (e.g., general or special purpose processors), firmware, and/or software embodied in a non-transitory computer-readable (storage) medium for execution by one or more processors to perform described functionality.

The description of the different advantageous arrangements has been presented for purposes of illustration and description, and is not intended to be exhaustive or limited to the examples in the form disclosed. Many modifications and variations will be apparent to those of ordinary skill in the art. Further, different advantageous examples may describe different advantages as compared to other advantageous examples. The example or examples selected are chosen and described in order to explain the principles of the examples, the practical application, and to enable others of ordinary skill in the art to understand the disclosure for various examples with various modifications as are suited to the particular use contemplated.

Different examples of the system(s), device(s), and method(s) disclosed herein include a variety of components, features, and functionalities. It should be understood that the various examples of the system(s), device(s), and method(s) disclosed herein may include any of the components, features, and functionalities of any of the other examples of the system(s), device(s), and method(s) disclosed herein in any combination or any sub-combination, and all of such possibilities are intended to be within the scope of the disclosure.

Thus, examples of the present disclosure relate to enumerated clauses (ECs) listed below in any combination or any sub-combination.

EC 1 is a computer-implemented method for identifying a heart condition in a non-human subject, the method comprising: receiving a medical image of the non-human subject; determining, by a processor executing a first machine-learning logic and based on the medical image, a dimensional feature of a heart of the non-human subject, wherein the first machine-learning logic is trained using medical image training data labeled with anatomical landmarks; receiving medical information associated with the non-human subject on a graphical user interface, the medical information including one or more of a species, an age, a weight, an output of a brain natriuretic peptide (BNP) test, and a murmur observation; determining, by the processor executing a second machine-learning logic and based on the medical information and the dimensional feature of the heart, a likelihood of a heart disease, wherein the second machine-learning logic is trained using heart disease training data and combinations of which are labeled with different stages of heart disease; and displaying the likelihood of the heart disease on the graphical user interface.

EC 2 is the method of EC 1, wherein: said receiving of the medical image comprises receiving one or more of an echocardiogram, an x-ray, a radiograph, and an ultrasound image.

EC 3 is the method of any of ECs 1-2, wherein said determining of the dimensional feature of the heart comprises: determining features in the medical image matching to the anatomical landmarks in the labeled training data; and performing a measurement calculation between selected features in the medical image.

EC 4 is the method of any of ECs 1-3, wherein said determining of the dimensional feature of the heart comprises determining a vertebral heart score.

EC 5 is the method of any of ECs 1-4, wherein said determining of the dimensional feature of the heart comprises determining an atrial measurement.

EC 6 is the method of any of ECs 1-5, wherein said determining of the dimensional feature of the heart comprises determining a ventricular left atrial size (VLAS) measurement.

EC 7 is the method of any of ECs 1-6, wherein said determining of the dimensional feature of the heart comprises determining a vertebral heart scale (VHS).

EC 8 is the method of any of ECs 1-7, wherein said receiving of the medical image comprises receiving a radiograph and an echocardiogram, and wherein said determining the dimensional feature of the heart comprises: determining a ventricular left atrial size (VLAS) measurement based on the radiograph; determining a left atrial to aortic ratio (LA/Ao) measurement based on the echocardiogram; and determining a left ventricular internal diameter at end-diastole (LVIDdN) measurement based on the echocardiogram.

EC 9 is the method of any of ECs 1-8, further comprising displaying the dimensional feature of the heart on a graphical user interface as a digital graphic overlaying the medical image on the graphical user interface.

EC 10 is the method of any of ECs 1-9, wherein said determining of the likelihood of the heart disease comprises determining a likelihood of a mitral valve disease.

EC 11 is the method of any of ECs 1-10, wherein said determining of the likelihood of the heart disease comprises determining a stage of the heart disease.

EC 12 is the method of any of ECs 1-11, wherein said displaying of the likelihood of the heart disease on the graphical user interface comprises: displaying a prediction of a stage of the heart disease; displaying a summary of the dimensional feature of the heart; and displaying interactive menus selectable to modify the graphical user interface to display a graph for trend analysis.

EC 13 is a server comprising: one or more processors; and non-transitory computer readable medium having stored therein instructions that when executed by the one or more processors, causes the server to perform functions comprising: receiving a medical image of a non-human subject; determining, by the one or more processors executing a first machine-learning logic and based on the medical image, a dimensional feature of a heart of the non-human subject, wherein the first machine-learning logic is trained using medical image training data labeled with anatomical landmarks; receiving medical information associated with the non-human subject on a graphical user interface, the medical information including one or more of a species, an age, a weight, an output of a brain natriuretic peptide (BNP) test, and a murmur observation; determining, by the one or more processors executing a second machine-learning logic and based on the medical information and the dimensional feature of the heart, a likelihood of a heart disease, wherein the second machine-learning logic is trained using heart disease training data and combinations of which are labeled with different stages of heart disease; and displaying the likelihood of the heart disease on the graphical user interface.

EC 14 is the server of EC 13, wherein said receiving of the medical image comprises receiving one or more of an echocardiogram, an x-ray, a radiograph, and an ultrasound image.

EC 15 is the server of any of ECs 13-14, wherein said determining of the dimensional feature of the heart comprises: determining features in the medical image matching to the anatomical landmarks in the labeled training data; and performing a measurement calculation between selected features in the medical image.

EC 16 is the server of any of ECs 13-15, wherein said receiving of the medical image comprises receiving a radiograph and an echocardiogram, and wherein said determining the dimensional feature of the heart comprises: determining a ventricular left atrial size (VLAS) measurement based on the radiograph; determining a left atrial to aortic ratio (LA/Ao) measurement based on the echocardiogram; and determining a left ventricular internal diameter at end-diastole (LVIDdN) measurement based on the echocardiogram.

EC 17 is a non-transitory computer readable medium having stored thereon instructions, that when executed by one or more processors of a computing device, cause the computing device to perform functions comprising: receiving a medical image of the non-human subject; determining, by the one or more processors executing a first machine-learning logic and based on the medical image, a dimensional feature of a heart of the non-human subject, wherein the first machine-learning logic is trained using medical image training data labeled with anatomical landmarks; receiving medical information associated with the non-human subject on a graphical user interface, the medical information including one or more of a species, an age, a weight, an output of a brain natriuretic peptide (BNP) test, and a murmur observation; determining, by the one or more processors executing a second machine-learning logic and based on the medical information and the dimensional feature of the heart, a likelihood of a heart disease, wherein the second machine-learning logic is trained using heart disease training data and combinations of which are labeled with different stages of heart disease; and displaying the likelihood of the heart disease on the graphical user interface.

EC 18 is the non-transitory computer readable medium of EC 17, wherein said determining of the dimensional feature of the heart comprises: determining features in the medical image matching to the anatomical landmarks in the labeled training data; and performing a measurement calculation between selected features in the medical image.

EC 19 is the non-transitory computer readable medium of any of ECs 17-18, wherein said receiving of the medical image comprises receiving a radiograph and an echocardiogram, and wherein said determining the dimensional feature of the heart comprises: determining a ventricular left atrial size (VLAS) measurement based on the radiograph; determining a left atrial to aortic ratio (LA/Ao) measurement based on the echocardiogram; and determining a left ventricular internal diameter at end-diastole (LVIDdN) measurement based on the echocardiogram.

EC 20 is the non-transitory computer readable medium of any of ECs 17-19, wherein functions further comprise displaying the dimensional feature of the heart on the graphical user interface as a digital graphic overlaying the medical image on the graphical user interface.

By the term "substantially" and "about" used herein, it is meant that the recited characteristic, parameter, or value need not be achieved exactly, but that deviations or variations, including for example, tolerances, measurement error, measurement accuracy limitations and other factors known to skill in the art, may occur in amounts that do not preclude the effect the characteristic was intended to provide. The terms "substantially" and "about" represent the inherent degree of uncertainty that may be attributed to any quantitative comparison, value, measurement, or other representation. The terms "substantially" and "about" are also utilized herein to represent the degree by which a quantitative representation may vary from a stated reference without resulting in a change in the basic function of the subject matter at issue.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

What is claimed is:

1. A computer-implemented method for identifying a heart condition in a non-human subject, the method comprising:

receiving a first medical image and a second medical image of the non-human subject;

determining, by a processor executing a first machine-learning logic and based on the first medical image and the second medical image, a first dimensional feature and a second dimensional feature of a heart of the non-human subject, wherein the first machine-learning logic is trained using medical image training data labeled with anatomical landmarks, wherein the first machine-learning logic programmatically identifies a first plurality of pixel points corresponding to the anatomical landmarks in the first medical image and wherein determining the first dimensional feature comprises calculating a vertebral heart scale (VHS) by performing measurements using the first plurality of pixel points of a longest axis of a cardiac silhouette and a short axis of the cardiac silhouette perpendicular to the longest axis, and programmatically transferring the measurements to a vertebrae count;

wherein the first machine-learning logic programmatically identifies a second plurality of pixel points corresponding to the anatomical landmarks in the second medical image and wherein determining the second dimensional feature comprises identifying from the second plurality of pixel points measurements of the heart across different phases of a cardiac cycle, including at least an end-diastole phase measurement and an end-systole phase measurement;

receiving medical information associated with the non-human subject on a graphical user interface, the medical information including one or more of a species, an age, a weight, an output of a brain natriuretic peptide (BNP) test, and a murmur observation;

determining, by the processor executing a second machine-learning logic and based on the medical information and the first dimensional feature and the second dimensional feature of the heart, a likelihood of a heart disease, wherein the second machine-learning logic is trained using heart disease training data and combinations of which are labeled with different stages of heart disease; and displaying the likelihood of the heart disease on the graphical user interface.

2. The method of claim 1, wherein said receiving of the first medical image and the second medical image comprises receiving one or more of an echocardiogram, an x-ray, a radiograph, and an ultrasound image.

3. The method of claim 1, wherein said determining of the first dimensional feature of the heart comprises:

determining features in the first medical image matching to the anatomical landmarks in the labeled training data; and performing a measurement calculation between selected features in the first medical image.

4. The method of claim 1, wherein said determining of the first dimensional feature of the heart comprises determining an atrial measurement.

5. The method of claim 1, wherein said determining of the first dimensional feature of the heart comprises determining a ventricular left atrial size (VLAS) measurement.

6. The method of claim 1, wherein said receiving of the first medical image and the second medical image comprises receiving a radiograph and an echocardiogram, and wherein said determining the first dimensional feature and the second dimensional feature of the heart comprises:

determining a ventricular left atrial size (VLAS) measurement based on the radiograph;

determining a left atrial to aortic ratio (LA/Ao) measurement based on the echocardiogram; and determining a left ventricular internal diameter at end-diastole (LVIDdN) measurement based on the echocardiogram.

7. The method of claim 1, further comprising:

displaying the first dimensional feature of the heart on the graphical user interface.

8. The method of claim 7, wherein said displaying of the first dimensional feature of the heart on the graphical user interface comprises displaying the first dimensional feature of the heart on the graphical user interface as a digital graphic overlaying the first medical image on the graphical user interface.

9. The method of claim 1, wherein said determining of the likelihood of the heart disease comprises determining a likelihood of a mitral valve disease.

10. The method of claim 1, wherein said determining of the likelihood of the heart disease comprises determining a stage of the heart disease.

11. The method of claim 1, wherein said displaying of the likelihood of the heart disease on the graphical user interface comprises:

displaying a prediction of a stage of the heart disease;

displaying a summary of the first dimensional feature of the heart; and displaying interactive menus selectable to modify the graphical user interface to display a graph for trend analysis.

12. A server comprising:

one or more processors; and non-transitory computer readable medium having stored therein instructions that when executed by the one or more processors, causes the server to perform functions comprising:

receiving a first medical image and a second medical image of a non-human subject;

determining, by the one or more processors executing a first machine-learning logic and based on the first medical image and the second medical image, a first dimensional feature and a second dimensional feature of a heart of the non-human subject, wherein the first machine-learning logic is trained using medical image training data labeled with anatomical landmarks, wherein the first machine-learning logic programmatically identifies a first plurality of pixel points corresponding to the anatomical landmarks in the first medical image and wherein determining the first dimensional feature comprises calculating a vertebral heart scale (VHS) by performing measurements using the first plurality of pixel points of a longest axis of a cardiac silhouette and a short axis of the cardiac silhouette perpendicular to the longest axis, and programmatically transferring the measurements to a vertebrae count;

wherein the first machine-learning logic programmatically identifies a second plurality of pixel points corresponding to the anatomical landmarks in the second medical image and wherein determining the second dimensional feature comprises identifying from the second plurality of pixel points measurements of the heart across different phases of a cardiac cycle, including at least an end-diastole phase measurement and an end-systole phase measurement;

receiving medical information associated with the non-human subject on a graphical user interface, the medical information including one or more of a species, an age, a weight, an output of a brain natriuretic peptide (BNP) test, and a murmur observation;

determining, by the one or more processors executing a second machine-learning logic and based on the medical information and the first dimensional feature and the second dimensional feature of the heart, a likelihood of a heart disease, wherein the second machine-learning logic is trained using heart disease training data and combinations of which are labeled with different stages of heart disease; and displaying the likelihood of the heart disease on the graphical user interface.

13. The server of claim 12, wherein said receiving of the first medical image and the second medical image comprises receiving one or more of an echocardiogram, an x-ray, a radiograph, and an ultrasound image.

14. The server of claim 12, wherein said determining of the first dimensional feature of the heart comprises:

determining features in the first medical image matching to the anatomical landmarks in the labeled training data; and performing a measurement calculation between selected features in the first medical image.

15. The server of claim 12, wherein said receiving of the first medical image and the second medical image comprises receiving a radiograph and an echocardiogram, and wherein said determining the first dimensional feature and the second dimensional feature of the heart comprises:

determining a ventricular left atrial size (VLAS) measurement based on the radiograph;

determining a left atrial to aortic ratio (LA/Ao) measurement based on the echocardiogram; and determining a left ventricular internal diameter at end-diastole (LVIDdN) measurement based on the echocardiogram.

16. A non-transitory computer readable medium having stored thereon instructions, that when executed by one or more processors of a computing device, cause the computing device to perform functions comprising:

receiving a first medical image and a second medical image of a non-human subject;

determining, by the one or more processors executing a first machine-learning logic and based on the first medical image and the second medical image, a first dimensional feature and a second dimensional feature of a heart of the non-human subject, wherein the first machine-learning logic is trained using medical image training data labeled with anatomical landmarks, wherein the first machine-learning logic programmatically identifies a first plurality of pixel points corresponding to the anatomical landmarks in the first medical image and wherein determining the first dimensional feature comprises calculating a vertebral heart scale (VHS) by performing measurements using the first plurality of pixel points of a longest axis of a cardiac silhouette and a short axis of the cardiac silhouette perpendicular to the longest axis, and programmatically transferring the measurements to a vertebrae count;

wherein the first machine-learning logic programmatically identifies a second plurality of pixel points corresponding to the anatomical landmarks in the second medical image and wherein determining the second dimensional feature comprises identifying from the second plurality of pixel points measurements of the heart across different phases of a cardiac cycle, including at least an end-diastole phase measurement and an end-systole phase measurement;

receiving medical information associated with the non-human subject on a graphical user interface, the medical information including one or more of a species, an age, a weight, an output of a brain natriuretic peptide (BNP) test, and a murmur observation;

determining, by the one or more processors executing a second machine-learning logic and based on the medical information and the first dimensional feature and the second dimensional feature of the heart, a likelihood of a heart disease, wherein the second machine-learning logic is trained using heart disease training data and combinations of which are labeled with different stages of heart disease; and displaying the likelihood of the heart disease on the graphical user interface.

17. The non-transitory computer readable medium of claim 16, wherein said determining of the first dimensional feature of the heart comprises:

determining features in the first medical image matching to the anatomical landmarks in the labeled training data; and performing a measurement calculation between selected features in the first medical image.

18. The non-transitory computer readable medium of claim 16, wherein said receiving of the first medical image and the second medical image comprises receiving a radiograph and an echocardiogram, and wherein said determining of the first dimensional feature and the second dimensional feature of the heart comprises:

determining a ventricular left atrial size (VLAS) measurement based on the radiograph;

determining a left atrial to aortic ratio (LA/Ao) measurement based on the echocardiogram; and determining a left ventricular internal diameter at end-diastole (LVIDdN) measurement based on the echocardiogram.

19. The non-transitory computer readable medium of claim 16, wherein the functions further comprise:

displaying the first dimensional feature of the heart on the graphical user interface as a digital graphic overlaying the first medical image on the graphical user interface.

* * * * *